United States Patent [19]
Crawford

[11] Patent Number: 4,709,333
[45] Date of Patent: Nov. 24, 1987

[54] METHOD AND APPARATUS FOR IMAGING IN THE PRESENCE OF MULTIPLE HIGH DENSITY OBJECTS

[75] Inventor: Carl R. Crawford, Milwaukee, Wis.

[73] Assignee: General Electric Company, Milwaukee, Wis.

[21] Appl. No.: 816,013

[22] Filed: Jan. 3, 1986

[51] Int. Cl.$^4$ ............................................. G06F 15/42
[52] U.S. Cl. ................................... 364/414; 378/901; 358/111
[58] Field of Search ................. 364/414, 521; 278/95, 278/901; 358/111; 378/901

[56] References Cited

U.S. PATENT DOCUMENTS

| | | | |
|---|---|---|---|
| 4,245,244 | 1/1981 | Lijewski | 378/99 |
| 4,590,558 | 5/1986 | Glover | 364/571 |
| 4,624,007 | 11/1986 | Muranushi | 378/99 |

OTHER PUBLICATIONS

"An algorithm for reduction of metal clip artifacts in CT constructions", *Medical Physics*, vol. 8, No. 6, Nov./Dec. 1981, G.H. Glover and N.J. Pelc.

Primary Examiner—Jerry Smith
Assistant Examiner—Gail Hayes
Attorney, Agent, or Firm—Mark L. Mollon; Douglas E. Stoner

[57] ABSTRACT

Method and apparatus for producing CT images in which localized regions ("rub-out" regions) of the original object are not reproduced in order to eliminate artifacts generated by objects within those regions. An operator defines rub-out regions encompassing objects to be removed. For each projection, the rub-out regions of the object are determined and then merged together. A baseline is calculated for each modified rub-out region. That information is then utilized to modify the projection set, in effect eliminating the object from the set. The modified projection set is then used to create a reconstructed image in the normal way.

7 Claims, 6 Drawing Figures

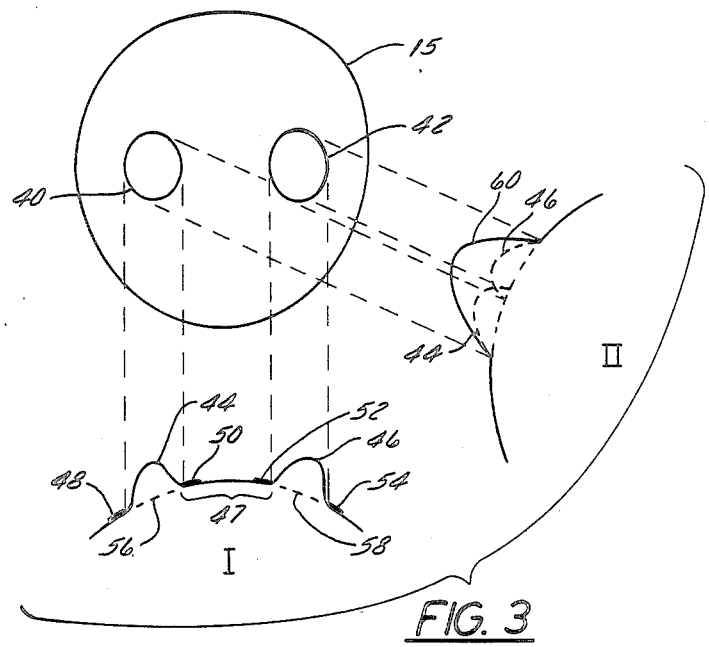
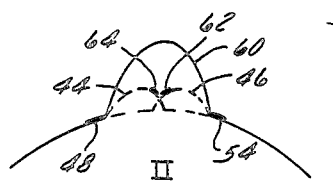
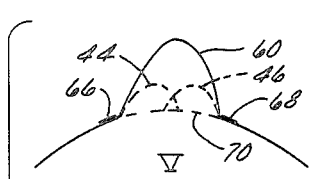
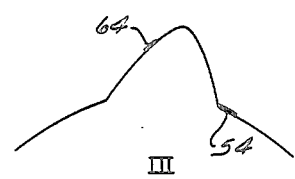
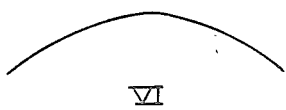
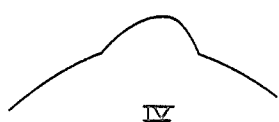
FIG. 3  FIG. 4  FIG. 5

METHOD AND APPARATUS FOR IMAGING IN THE PRESENCE OF MULTIPLE HIGH DENSITY OBJECTS

BACKGROUND OF THE INVENTION

This invention relates to computed tomography (CT) and more particularly to a method and apparatus for removing artifacts from CT images caused by the presence of multiple high density structures in the object region being imaged.

Modern computed tomography has provided diagnostic images containing information which was either not available or difficult to interpret using prior imaging techniques. At the same time, structures in or on the body which had previously not created serious imaging problems have led to artifacts which made CT images difficult to interpret.

One example of such structures is that of surgical clips present within the slice to be imaged. Other examples include dental fillings, contrast materials, and prostheses. Such objects are typically of very high density as compared to the surrounding tissue and are often found to create artifacts known as "starburst." Such artifacts limit the diagnostic utility of the CT image. It is therefore desirable to provide a method for eliminating or reducing such artifacts.

The general basis for many artifact removal methods which rely on modification of projection data to produce a corrected image is the assumption that the detector readings corresponding to the line integrals (which comprise the projection measurements) through a high-density object(s) are invalid and, hence, cannot be used in the reconstruction algorithm. This method of artifact correction, in effect, removes the high-density object because the projection data corresponding to the object is removed prior to reconstruction of a corrected image. Such methods are to be distinguished from techniques such as that disclosed in U.S. Pat. No. 4,075,700 in which image features which are not of interest are removed by operating on image data which is derivable only after processing the projection measurements. In accordance with the technique disclosed in the aforeidentified patent, the position coordinates of the features to be removed are identified, and the corresponding absorption coefficients are assigned zero or maximum values, thereby erasing features of little interest. Techniques of this kind have been found ineffective in removing artifacts due to the presence of high density objects in the field of view, primarily for the reason that the operation is cosmetic and does not correct the underlying errors in the projection data.

In accordance with the artifact removal methods relying on the correction of the projection data, itself, rather than modification of image data, it is necessary to identify which projection measurements are defective. This can be accomplished by performing a preliminary reconstruction of the projection data using known reconstruction techniques, such as filtered back projection. The preliminary image can be displayed on a cathode ray tube (CRT). The starburst artifacts will be obvious to a user, since they appear as high-density regions having streaks and other shading artifacts which originate from the regions in the image where the high-density object are centered. These regions can be identified by using a light pen (similar to that described in the afore-identified U.S. Pat. No. 4,075,700) to draw a boundary around the image of the object. Alternatively, a geometrical region of interest (ROI), such as a circle, can be positioned around the object using a trackball control feature commonly available in modern CT scanners. For example, U.S. Pat. No. 4,245,244, assigned to the same assignee as the present invention, discloses and claims a device for delineating zones in a video image display under the control of a trackball. Another example of a cursor generator for use in computerized tomography and other image display systems is disclosed and claimed in U.S. Pat. No. 4,259,725, which is also assigned to the same assignee as the present application.

Once the high density objects present in the preliminary image are outlined in the manner described above, well-known procedures can be used to determine which projection measurements correspond to readings through the object. For a given computerized tomography scanner geometry (e.g., source-to-isocenter distance, source-to-detector distance, the fan angle of the X-ray beam, and the number of detectors in the detector array), it is possible to determine which projection measurements in each projection contributed to the shadow of the object on the detector array of the high-density object. If there are multiple regions of interest defined, indicating the presence of more than one high-density object, then the detector measurements contributing to each region can be independently identified.

It will be beneficial to consider some additional prior art methods of producing a corrected image given the fact that some of the projection measurements are unusable and, therefore, may be considered as missing. This is important because widely used filtered back projection algorithms for reconstructing CT images will not work satisfactorily because of the requirement that all of the projection data be available. Mathematically, it is well known that if some fraction of the projection data is available, then all of the projection data can be calculated. This can be accomplished because of the consistency of the Radon transform of the object. However, methods relying on this principle are extremely computationally expensive and unstable when any noise is present.

Another known method to reconstruct the partial projection data is to use iterative reconstruction methods. These methods are known as algebraic reconstruction techniques and are frequently referred to as ART. The advantage of the ART methods over filtered back projection is that they can work reasonably well with partial projection data and, hence, can be used to remove artifacts. It is believed that ART is a highly effective reconstruction method for removing artifacts in situations where some of the projection data is corrupted and cannot be used. However, a drawback of ART is that it is extremely computationally expensive and unlike filtered back projection difficult to implement in high-speed form, requiring special-purpose hardward to implement the reconstruction algorithm.

It is therefore apparent that it is desirable to obtain a computationally inexpensive algorithm for the purpose of removing artifacts from images containing high-density objects. One of the preferred methods would be to use filtered back projection in the reconstruction process due to the fact that many of the commercially available computerized tomography scanners have hardware to support this method. The filtered backprojection method requires, however, that all of the projection measurements be available.

U.S. Pat. No. 4,178,510 relates to the use of filtered back projection reconstruction methods for constructing an image when one or more detectors in the detector array are not operational and therefore the data therefrom is unusable and must be replaced. In accordance with this method, the readings corresponding to the inoperative detectors can be obtained by interpolation of data from valid detector readings on either side of the inoperational detectors, enabling the repair of such detectors to be performed at a later, more convenient time. The interpolation used can be either linear interpolation or higher order. Higher order interpolation is also frequently referred to as polynominal completion.

The method described in the aforeidentified patent has similarities to techniques used for artifact removal. In one situation, the projection data is missing because the detectors are inoperative, while in the other situation the detectors are operative but the data is unusable (and therefore may be considered as missing or unavailable). It will be apparent to those skilled in the art that in the situation of artifact removal simple interpolation can be used to remove the unusable data. A difference between the two situations, however, is that in the inoperative detector case the same detectors are inoperative in every projection. In the artifact removal case, the detectors which sense the unusable data will change from view to view as the X-ray source and detector rotate about the object being imaged. In the latter situation, the actual projection measurements, which are corrupted and must be replaced, can be determined by using the region-of-interest feature described hereinabove. This method shall hereinafter be referred to as simple polynomial completion algorithm. A difficulty which arises with the simple polynomial completion algorithm is that when other high-density objects are in the field of view (FOV), such as bone associated with the spinal column, streak artifacts will be generated in the region of the corrected image between the position where the removed object was and the other high-density objects present in the image.

The paper entitled "An Algorithm for the Reduction of Metal Clip Artifacts in CT Reconstruction," in *Medical Physics*, Vol. 8, November/December (1981), pp 789-807, G. Glover and N. Pelc, presents an improved method which reduces some of the induced streak artifacts. This method utilizes local averages of the projection data (after the object to be removed is mathematically centered at the isocenter of the system) to increase the object-to-background ratio. This process, in effect, creates a base on which to do the linear interpolation. This method is known as the rubout algorithm for artifact removal. An improvement of the rubout algorithm for removing artifacts due to objects with extremely high density is also disclosed in the above-identified article. In this method, reprojections of the other high-density objects in the field of view are subtracted from the original, unmodified projection set before the application of the rubout algorithm. The rubout algorithm is disclosed and claimed in commonly assigned U.S. patent application Ser. No. 335,973, filed Dec. 30, 1981.

Some of the aforementioned artifact removal methods do not work satisfactorily when multiple high-density objects are present in the field of view (FOV) and need to be removed. The previous methods were applied sequentially on the multiple objects to be removed and failed for this reason, as will be more fully disclosed hereinafter.

In view of the foregoing, it is a general object of the present invention to improve the quality of this class of CT images by minimizing the effect of image artifacts created by multiple high density objects located in the field of view.

Another object of the prsent invention is to reduce artifacts caused by the presence of multiple, sharp, localized discontinuities, such as surgical clips in the field of view without degrading the CT image by introducing other artifacts.

A further object of the present invention is to reduce artifacts caused by the presence of multiple high-density objects, such as prostheses and dental fillings, without resorting to computationally expensive reconstruction algorithms.

SUMMARY OF THE INVENTION

A method and apparatus are provided for removing a plurality of high density objects from a CT image. The method includes the steps of exposing a body having a plurality of high density objects therein to penetrating radiation at a plurality of angles about the body and detecting the radiation passing through the body at a plurality of angles to create a projection set made up of a plurality of projections, each projection being made up of a plurality of elements. The plurality of projections is used to reconstruct an initial image in which a user defines a plurality of regions encompassing the high density objects to be removed from each projection. The projection elements corresponding to paths through the defined regions are marked so as to form a plurality of swaths, including a baseline projection element adjacent to both extremes of each of said swaths. The swaths sharing the same projection elements are combined. The combined swath projections in each of the swaths is rendered consistent with the projection elements lying outside the swaths so as to create a corrected projection which are used to reconstruct an image.

BRIEF DESCRIPTION OF THE DRAWINGS

The features of the invention believed to be novel are set forth with particularity in the appended claims. The invention itself, however, both as to its organization and method of operation, together with further objects and advantages thereof, may best be understood by reference to the following description taken in conjunction with the accompanying drawings in which:

FIG. 3 illustrates an object having two prostheses situated therein and two exemplary projection sets;

FIG. 4 illustrates application of a conventional polynomial interpolation technique to a projection set having corrupted data due to presence of multiple prostheses in the object image;

FIG. 5 illustrates the application of the polynomial interpolation method in accordance with the invention to remove the corrupted measurements in a projection set.

DETAILED DESCRIPTION OF THE INVENTION

Figure 1:
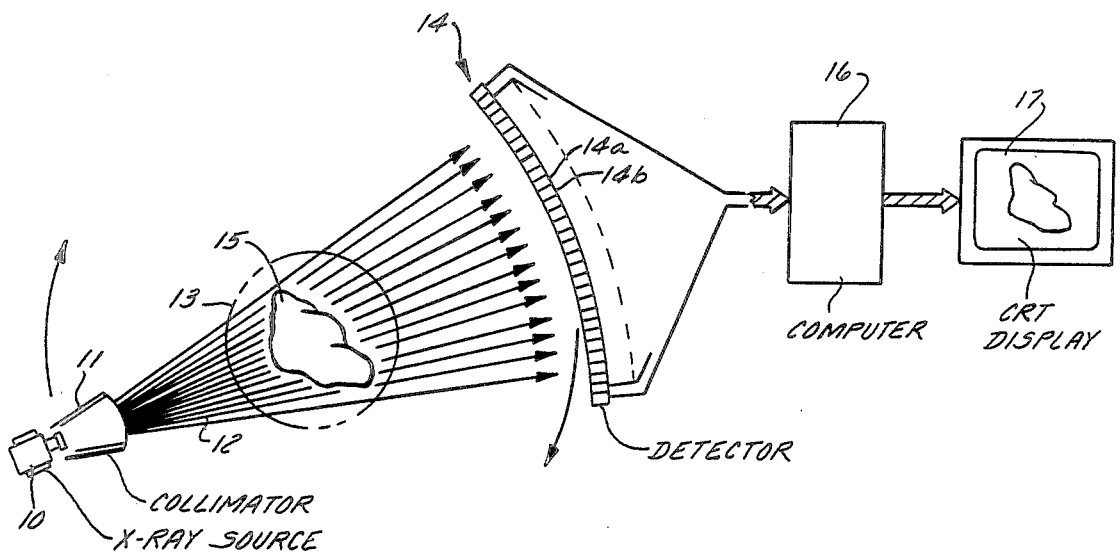
FIG. 1 is a schematic view illustrating the major elements of a CT scanner.

Turning now to the drawings, FIG. 1 schematically illustrates the major elements of a CT scanner. The scanner includes a source of penetrating radiation 10, very often in the form of a rotating anode X-ray tube. The radiation produced by the X-ray tube 10 is collimated at 11 to produce a thin fan beam of radiation 12 which is projected through a patient aperture 13 toward an X-ray detector array 14. A body to be examined, such as a patient 15, is positioned, within the patient aperture 13 in the path of the fan beam of X-rays 12 such that the beam passing through the body is attenuated in dependence on the density of the objects encountered. As a result, each detector cell 14a, 14b, etc. produces an electrical signal which is dependent on the intensity of the radiation received within the cell. The signals thus produced are therefore measures of the attenuation of the X-ray beam by the portion of the body through which it passed.

In operation, X-ray readings are taken from each cell at a plurality of angular positions with respect to the patient, as the source and detector array are rotated about the patient aperture. Each set of readings at a particular angle is often referred to as a projection or view. The projection can be considered to be made up of a number of elements (projection measurements), each element representing one of the detector readings. The readings thus produced for each view are digitized and fed to a reconstruction computer 16 which can use one of a number of available algorithms (e.g., such as ART, or filtered backprojection) to produce the image of the cross section traversed by the fan beam. The image can be displayed on a CRT 17, or alternatively can be used to create a film for further study by a diagnostician.

FIG. 1 shows a scanner geometry which has come to be known as rotate-rotate, in which the source is fixed with respect to the detector array, and they rotate in unison about the patient aperture. The invention to be described herein is applicable not only to this geometry, but to other CT geometries as well, the common characteristic being the creation of a plurality of projections made up of a plurality of elements.

Figure 2:
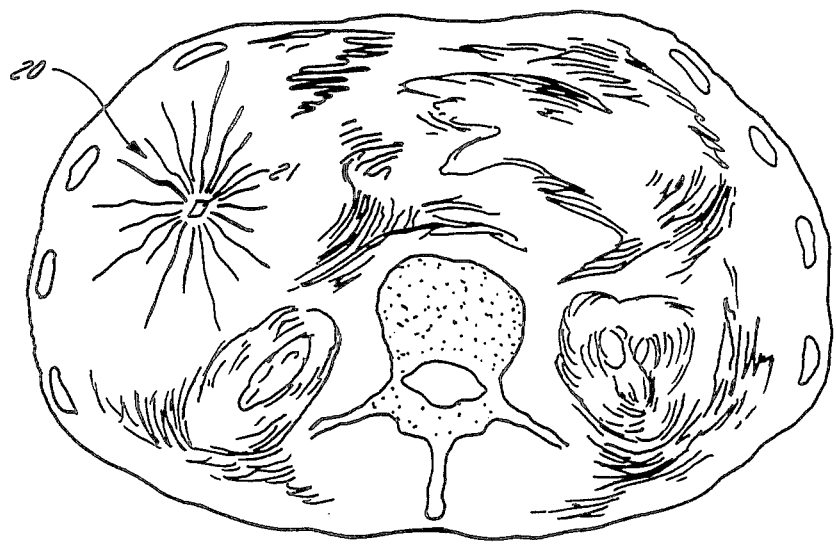
FIG. 2 is a reproduction of a portion of a CT image illustrating one starburst artifact.

Turning to FIG. 2, there is shown a portion of a CT image of the body including a starburst artifact 20 shown emanating from the site of a surgical clip 21. As can be seen, the artifact appears as a series of streaks which emanate radially from the site of the clip. Of course, a CT image of a patient having multiple high-density objects in the area imaged would contain multiple starburst artifacts (not shown to preserve clarity of the Figure) similar to artifact 20.

The streak artifacts may, in principle, be caused by various effects such as undersampling, beam hardening, partial volume effects, detection system nonlinearities due, for example, to underranging of the electronics, or to motion.

As disclosed in the above-identified U.S. patent application Ser. No. 335,973, it has been discovered through study and experiment that the artifact illustrated in FIG. 2 is primarily caused by motion. Subtle sudden motion of a high contrast, high density object such as a surgical clip would manifest itself in the constructed image as a streak oriented in the direction of the projection being measured at the time of the motion. Movement of even less than a resolution distance is sufficient to cause a significant artifact. Normal metabolic activity can cause involuntary displacement of the metallic clip in rhythm with peristaltic or circulatory functions. If the metal object had a pulsatile motion at the heartbeat rate, one would expect an inconsistency in the scan data projection set and a streak in the reconstruction at each of those view angles where the object was displaced—of the order of 10 during a 9.8 sec. scan such as that in FIG. 2. Only slight differential motion would be required in order to produce such streaks since the metal object, if faithfully reconstructed, would have a CT number of several thousand. These characteristics are descriptive of the artifact seen in FIG. 2.

As will be appreciated from the following description, the present invention eliminates the artifact (as well as the image of the clip or source of the artifact) whether or not it is caused by motion. Additionally, while the prior art provides methods to remove artifacts from images due to the presence of one high-density object, in accordance with the present invention a more robust algorithm is provided which works in the presence in the field of view of multiple high-density objects.

In accordance with the invention, projections which have been "contaminated" by high density objects are rendered consistent by "removing" the contaminations from the projection set and using the modified projection set for reconstructing an image with substantially reduced artifacts. Ideally, the rubout regions should be a small percentage of the total field of view so that only a small number of projection measurements are involved. The approach is to render the elements or detector readings within the rubout regions consistent (in the Radon sense) with the remaining elements such that the CT image can be reconstructed in the normal way using, in the preferred embodiment, filtered backprojection.

The basis of the new method lies in the fact that polynomial interpolation applied conventionally to projection sets having data corrupted by the presence of multiple high-density objects fails because at certain projection angles the unaffected projection measurements used to form the base line for the interpolation correspond, themselves, to corrupted projection measurement readings through other high-density objects. Referring to FIG. 3 there is shown a schematic representation of object 15 having uniform low density and having disposed therein by way of example two high-density objects designated 40 and 42 which are the source of starburst artifacts in the absence of proper corrections to the projection data. In the projection of the object depicted at I in FIG. 3, the projection measurements corresponding to paths through objects 40 and 42 are identified by reference numbers 44 and 46, respectively. In this case, if sufficient uncorrupted data is available in the portion of the projection designated 47, correction of the projection data can be accomplished using conventional polynomial interpolation techniques. Such correction is achieved by using uncorrupted projection measurement data (e.g., that designated 48 and 50, and 52 and 54, on either side of projections 44 and 46, respectively) as a baseline for the interpolation to calculate projection measurements which will replace the corrupted measurements in regions 56 and 58. Similar corrections are made to corrupted projection measurements in other projections so that when the original data is discarded and the new data is used in the image reconstruction, artifacts are eliminated from the resulting image.

A problem which arises and which is not addressed by the prior art methods is shown at II. in FIG. 3. At this projection angle, projections (44 and 46) of the high-density objects overlap so that corrupted measurements now comprise a larger portion 60 of the projection. Application of the conventional interpolation method to this situation, as will be discussed next with reference to FIG. 4, does not provide a satisfactory correction.

Referring now to FIG. 4 at II., application of the first conventional correction to projection 44 requires interpolation using as a baseline projection measurements in regions 48 and 62 to either side of projection 44. However, because the data at region 62 is part of the corrupted and therefore unusable data which forms part of projection 46, the resulting fit will be generally as shown at III in FIG. 4 and not as in 56 shown at I (FIG. 3). Continuing with the conventional approach, a second interpolation using the projection data as a baseline at regions 54 and 64 is used to calculate the correction for the corrupted projection measurements at 46. This application yields as a final result the projection set shown at IV. Reconstruction of the data using filtered backprojection to construct an image using the resulting projection set shown at IV will result, as will be apparent to those skilled in the art in an image having objectionable artifacts similar to those that were present before any correction was applied.

It has been recognized by Applicant herein that artifacts, due to the presence of multiple high-density objects in the field of view, particularly in the situations similar to that depicted at II in FIG. 3, can be reduced by considerating simultaneously the projection data in support regions 48, 50, 52 and 54 (FIG. 1). If the projections and the support regions do not overlap, then the conventional interpolation method can be invoked to fit the projection data as described above with reference to FIG. 3. However, when projections and/or the support regions overlap as shown in II, FIG. 3, the interpolation should be invoked on the union 60 of the projection of the combined projection regions 44 and 46. In this case, support regions 66 and 68, as indicated in FIG. 5, on either side of the union region 60 are used to calculate the replacement projection data. This results in new projection measurements designated 70 at V and as shown in corrected form at VI in FIG. 5. Unlike the conventional method described with reference to FIG. 4, the inventive method yields in a single interpolation step a corrected projection set such as that depicted at VI. Data corrected in this manner when reconstructed using backprojection methods result in a corrected image in which starburst artifacts are absent and no streak artifacts are introduced between the two removed high-density objects.

In general the union operation and interpolation are performed as follows. The user places in an uncorrected image regions of interest around high-density objects to be removed from the image. Usually a circular or an elliptical region of interest is used. Given the angle of the projection used and the geometry of the CT scanner, the projection of a region of interest, i, onto the detector array can be determined in a well-known manner. The left-most and right-most detectors are denoted $L_i$ and $R_i$, respectively. Let "b" be number of detectors in the base polynomial. Then $L_i - b = L_i'$ and $R_i + b = R_i'$ are the left and right edges of the potential polynomial completion region. Then, for each pair of regions i and J, where J is $\neq$ to i, if $R_i' < L_J'$ or $L_i' > R_J'$, then the two regions do not overlap. If they do overlap, the i'th region is replaced with $R_i' = \max (R_i', R_J')$ and $L_i' = \min (L_i', L_J)$ and the J'th region is dropped. The process continues until all pairwise combinations have been considered.

The method of the invention may be summarized as follows. The original (that is, the uncorrected or unmodified) projection data is reconstructed using, in a preferred embodiment, filtered backprojection and the resulting image, including any starburst artifacts contained therein, is displayed on the CRT display device 17 shown in FIG. 1. The user then identifies by outlining the portion of the uncorrected image using a light pen or a region of interest feature the high-density objects displayed. Using the information obtained through the light pen or the region of interest defined by the trackball, it is possible to identify the detectors corresponding to the projection measurements through the identified regions. The projection measurements identified in this manner are marked and will be referred to as rubout regions. The rubout regions are examined to see if they overlap or are too close together. Too close together is defined to mean that the number of detectors whose data is uncorrupted between the two rubout regions is less than the number of projection measurements required form a baseline needed to perform polynomial interpolation. If in fact the rubout regions are found to be too close together, they are combined in a step called the union of the rubout regions. Thus, if there were N rubout regions prior to the union step, then there will be at least one and not more than N regions after the union operation. Simple polynomial completion is then used in the manner described above to find a fit for the data in the rubout region resulting from the union operation. The corrected projections are then reconstructed using, in the preferred embodiment, filtered backprojection. If the level of artifact reduction is not sufficient, then the foregoing steps can be iteratively repeated.

Optionally, subsequent to the step of identifying the high-density objects in an uncorrected image but before the step of determining the corresponding projection measurements through the identified regions, the original uncorrected image less the identified regions, is reprojected and subtracted from the original projection data. If this step is employed, then subsequent to the step of fitting the data using simple polynomial completion, the reprojections should be added back prior to reconstructing a corrected image.

The computational steps of the above method can be performed on readily available digital computers. The preferred embodiment of such a computer is the Data General Eclipse 140 operating in conjuction with a Floating Point Systems AP-100 Array Processor.

Figure 6:
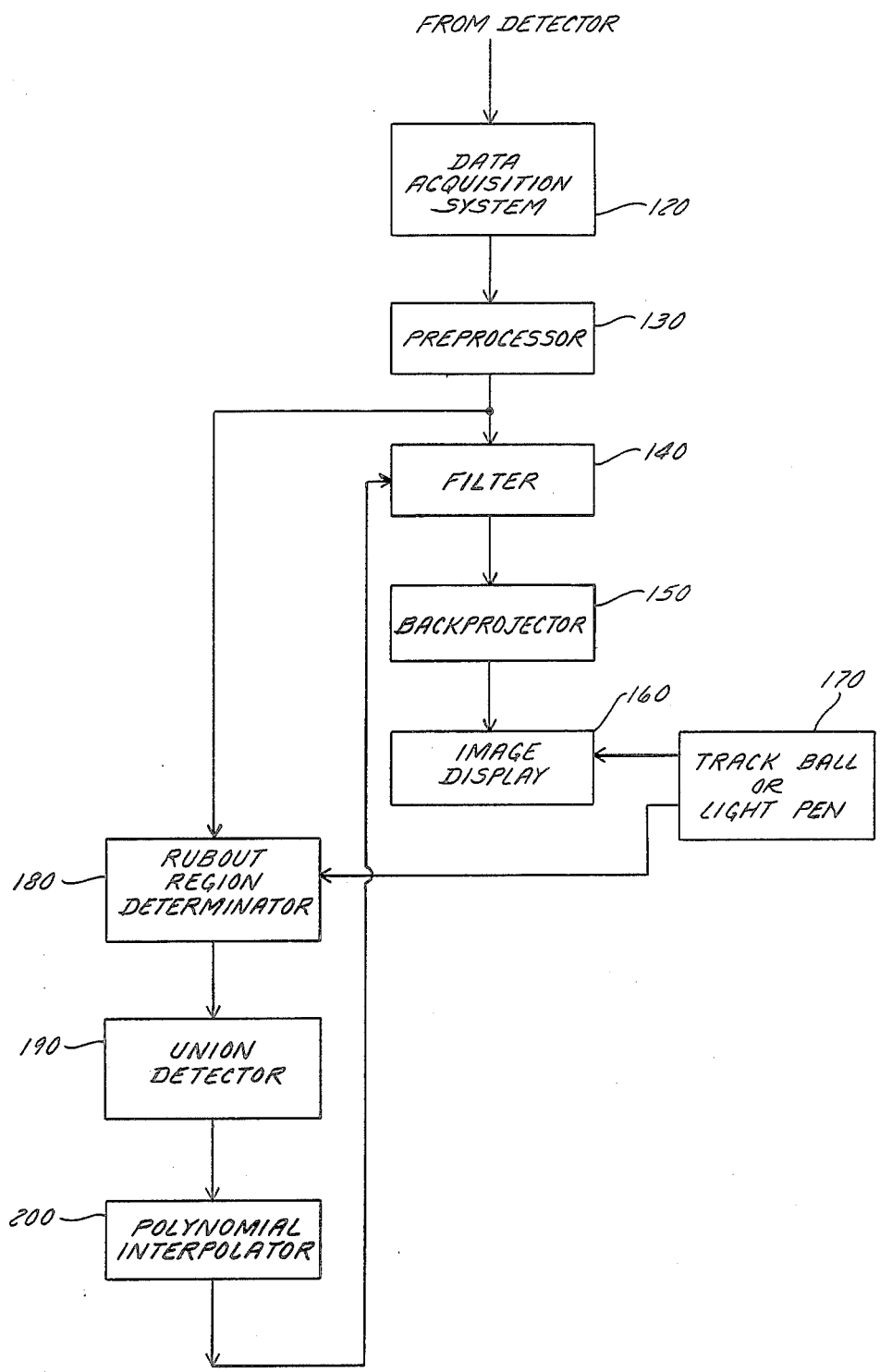
FIG. 6 illustrates in block-schematic form an apparatus suitable for practicing the invention.

In addition to the inventive method described above, the present invention also encompasses apparatus including computational processor means and means for creating projections including a source of radiation and a detector array, as shown in FIG. 1. Further aspects of the apparatus will be described with reference to FIG. 6 in which there is shown a data acquisition system (DAS) 120 coupled to the detector array shown in FIG. 1 for receiving the resulting electrical signals which are proportional to the amount of radiation received at the detector. The DAS operates to amplify the output of the detector and to digitize the electrical signals for further processing. The digitized signals are applied to preprocessing means 130 where, in accordance with methods well known to the art, they are processed to provide projection measurements. Filter means 140 and backprojector means 150 are used to implement in a well-known manner the filter backprojection reconstruction algorithm. The resulting uncorrected image is displayed on image display device 160. The operator can identify, using a light pen or trackball, as described hereinabove, the high-density objects displayed in the uncorrected reconstructed image. The operator can interactively perform this step using trackball means or light pen designated at 170. The information derived using the light pen or trackball is applied to the rubout region determining means 180. The other input to the rubout region determination means are the preprocessed projections produced by preprocessing means 130. For each preprocessed projection, the projection measurements corresponding through two paths through the identified high-density regions are marked. Union-forming means 190 is used to determine which marked projection measurements overlap or are close to overlapping thereby leaving insufficient uncorrupted projection measurements to use in the interpolation. The identified overlapping or close to overlapping regions are merged together to form a new set of marked projection measurements. Simple polynomial completion means 200 is then used to fit the projection data in the marked region by using the projection measurements on either side of each marked region to fit a polynomial to the adjacent readings. The corrected projection measurements are then applied back to the filter means 140 and backprojection means 150 and are used to reconstruct the corrected image which is applied to image display 160.

While this invention has been described with reference to particular embodiments and examples, other modifications and variations will occur to those skilled in the art in view of the above teachings. Accordingly, it should be understood that within the scope of the appended claims the invention may be practiced otherwise than is specifically described.

The invention claimed is:

1. A method for removing a plurality of high-density objects from a CT image comprising the steps of:
   (a) exposing a body having a plurality of high-density objects located therein to penetrating radiation at a pluarality of angles about the body;
   (b) detecting radiation passing through said body at a plurality of angles to create a projection set made up of a plurality of projections, each projection being made up of a plurality of elements;
   (c) reconstructing an initial image from said plurality of projections;
   (d) defining in said initial image regions encompassing said high-density objects to be removed for each projection;
   (e) marking projection elements corresponding to radiation paths through said defined regions forming a plurality of swaths of marked projection elements, including a baseline projection element adjacent to both extremes of each said swaths;
   (f) combining swaths that share the same projection elements;
   (g) rendering consistent for each of said combined swaths projection elements in said combined swaths with said projection elements lying outside said swaths so as to create corrected projections; and
   (h) reconstructing an image using said corrected projections.

2. The method of claim 1 wherein said step of rendering consistent comprises the step of using polynomial completion.

3. The method of claim 2 wherein said step of polynomial completion comprises linear interpolation.

4. Apparatus for removing a plurality of high-density objects from a CT image comprising:
   means for exposing a body having a plurality of high-density objects located therein to penetrating radiation at a pluraltiy of angles about the body;
   means for detecting radiation passing through said body at a plurality of angles to create a projection set made up of a plurality of projections, each projection being made up of a plurality of elements;
   means for reconstructing an initial image from said plurality of projections;
   means for defining in said initial image regions encompassing said high-density objects to be removed for each projection;
   means for marking projection elements corresponding to radiation paths through said defined regions forming a plurality of swaths of marked projection elements, including a baseline projection element adjacent to both extremes of each said swaths;
   means for combining swaths that share the same projection elements;
   means for rendering consistent for each of said combined swaths projection elements in said combined swaths with said projection elements lying outside said swaths so as to create corrected projections; and
   means for reconstructing an image using said corrected projections.

5. A method for removing a plurality of high-density objects from a CT image comprising the steps of:
   (a) exposing a body having a plurality of high-density objects located therein to penetrating radiation at a plurality of angles about the body;
   (b) detecting radiation passing through said body at a plurality of angles to create a projection set made up of a plurality of projections, each projection being made up of a plurality of elements;
   (c) reconstructing an initial image from said plurality of projections;
   (d) defining in said initial image regions encompassing said highdensity objects to be removed for each projection;
   (e) calculating a selective reprojection of said initial image excluding said identified object regions;
   (f) subtracting said selective reprojections from said projection set in said step (b).
   (g) marking projection elements corresponding to radiation paths through said defined regions forming a plurality of swaths of marked projection elements, including a baseline projection element adjacent to both extremes of each said swaths;
   (h) combining swaths that share the same projection elements;
   (i) rendering consistent for each of said combined swaths projection elements in said combined swaths with said projection elements lying outside said swaths so as to create corrected projections;
   (j) adding said selective reprojections to said corrected projections to create a merged projection; and
   (k) reconstructing an image from all of said merged projections.

6. The method of claim 5 wherein said rendering step employes polynomial completion.

7. The method of claim 6 wherein said polynomial completion is achieved by linear interpolation.

* * * * *